United States Patent [19]

Wiesenfeldt et al.

[11] Patent Number: 5,064,962

[45] Date of Patent: Nov. 12, 1991

[54] DIAMINOTHIOPHENES

[75] Inventors: Matthias Wiesenfeldt, Mutterstadt; Karl-Heinz Etzbach, Frankenthal, both of Fed. Rep. of Germany

[73] Assignee: BASF Aktiengesellschaft, Ludwigshafen, Fed. Rep. of Germany

[21] Appl. No.: 473,471

[22] Filed: Feb. 1, 1990

[30] Foreign Application Priority Data

Feb. 23, 1989 [DE] Fed. Rep. of Germany ....... 3905577

[51] Int. Cl.$^5$ ........................................... C07D 333/38
[52] U.S. Cl. .................................... 544/300; 544/316; 544/60; 544/146; 544/379; 546/284; 546/212; 548/136; 548/327; 548/374; 548/465; 548/468; 548/336; 548/527; 549/60; 549/61; 549/59
[58] Field of Search .................. 549/61; 544/300, 316; 548/136, 327, 374, 465, 468; 546/284

[56] References Cited

FOREIGN PATENT DOCUMENTS 583224 12/1976 Switzerland .

OTHER PUBLICATIONS

Gewald et al., Chemical Abstracts, vol. 77, No. 151786b (1972).
*Organic Chemistry*, 4th Ed., Morrison and Boyd, (1983), p. 1272, Allyn and Bacon, Inc.
J. Prakt. Chem., vol. 328, pp. 459-464, 1986, K. Gewald et al., "Substituierte 3,4-Diamino-Thieno(2,3-b)Pyrrole".
J. Chem. Soc. Perkin Trans. I, 1986, pp. 1171 to 1179, B. R. Fishwick et al., "Bromonitromethane-A Versatile Electrophile".
Monatsh. Chem., vol. 112, pp. 1393 to 1404, K. Gewald et al., "Zur Chemie Der 4-Aminothiazolin-2-Thione".

*Primary Examiner*—Mukund J. Shah
*Assistant Examiner*—Philip I. Datlow
*Attorney, Agent, or Firm*—Oblon, Spivak, McClelland, Maier & Neustadt

[57] ABSTRACT

Diaminothiophenes of the formula

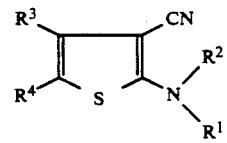

or tautomers thereof, where
$R^1$ and $R^2$ are each hydrogen or together are

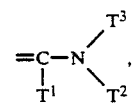

where $T^1$ is hydrogen, alkyl or phenyl, $T^2$ and $T^3$ are, independently of one another, alkyl or phenyl, or $T^2$ and $T^3$ together with the nitrogen linking them are a heterocyclic radical,
$R^3$ is substituted amino and
$R^4$ is alkanoyl, benzoyl, cyano, nitro or

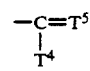

where $T^4$ is hydrogen, alkyl or phenyl and $T^5$ is the radical of a primary amine or of an active methylene compound, are prepared as described. The present diaminothiophene compound is useful in the synthesis of dyes, crop protection agents and pharmaceuticals.

1 Claim, No Drawings

DIAMINOTHIOPHENES

The present invention relates to novel diaminothiophenes of the formula I

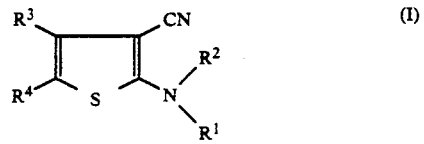

or tautomers thereof, where
R$^1$ and R$^2$ are each hydrogen or together are

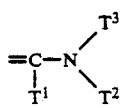

where T$^1$ is hydrogen, C$_1$–C$_4$-alkyl or phenyl, and T$^2$ and T$^3$ are identical or different and each, independently of one another, is C$_1$–C$_4$-alkyl, C$_5$–C$_7$-cycloalkyl or phenyl or T$^2$ and T$^3$ together with the nitrogen linking them are a 5- to 7-membered saturated heterocyclic radical which can contain further hetero atoms, R$^3$ is C$_1$–C$_{20}$-mono- or dialkylamino, C$_2$–C$_{10}$-mono- or dialkylamino whose alkyl is substituted and/or interrupted by one or more oxygens, C$_3$–C$_8$-cycloalkylamino, adamantylamino, C$_2$–C$_{12}$-mono- or dialkenylamino, C$_3$–C$_{12}$-alkynylamino, N-(C$_1$–C$_5$-alkyl)-N-phenylamino, pyrrolidino, piperidino, morpholino, thiomorpholino, piperazino, N-(C$_1$–C$_4$-alkyl)piperazino, hexamethyleneimino, 1-imidazolyl, 1-pyrazolyl, substituted or unsubstituted phenylamino, pyridylamino, thienylamino, hydrazino, C$_1$–C$_4$-mono- or dialkylhydrazino or phenylhydrazino and R$^4$ is C$_1$–C$_6$-alkanoyl, benzoyl, cyano, nitro or

where T$^4$ is hydrogen, C$_1$–C$_4$-alkyl or phenyl, and T$^5$ is the radical of an active methylene compound, or hydroxyimino or N-X where X is C$_1$–C$_{20}$-alkyl which can be substituted and/or interrupted by one or more oxygens, substituted or unsubstituted C$_3$–C$_6$-alkenyl, substituted or unsubstituted C$_3$–C$_6$-alkynyl, substituted or unsubstituted C$_3$–C$_{10}$-cycloalkyl, substituted or unsubstituted phenyl, pyridyl, C$_1$–C$_4$-alkoxycarbonylmethyl, amino, C$_1$–C$_4$-dialkylamino or phenylamino.

2,4-Diaminothiophene derivatives which have a substituted amino in position 2 and an unsubstituted amino in position 4 have been disclosed (see, for 10 example, J. Prakt. Chem. 326 (1986) 459 to 464; J. Chem. Soc. Perkin Trans. I (1986) 1171 to 1179 or Monatsh. Chem. 112 (1981) 1391 to 1404). Furthermore, CH-A 583,224 describes the preparation of 2,4-diamino-3,5-dicyanothiophene. The said diaminothiophenes are, however, not especially suitable diazo components for the preparation of azo dyes.

The object of the present invention was to prepare novel diaminothiophenes which have an unsubstituted amino in position 2 and a substituted amino in position 4.

In accordance with this, we have found the diaminothiophenes of the formula I defined above.

All the alkyls and alkenyls in the abovementioned formula I can be both straight-chain and branched.

When alkyls which are interrupted by one or more oxygens occur in the formula I, they are preferably interrupted by 1 to 3, in particular 1 or 2, oxygens.

Examples of suitable substituents for phenyls in the formula I are C$_1$–C$_4$-alkyl, C$_1$–C$_4$-alkoxy, halogen, in particular chlorine or bromine, nitro, hydroxyl, amino, C$_1$–C$_4$-dialkylamino, carboxyl or C$_1$–C$_4$-alkanoyl.

Examples of suitable substituents for alkyls in the formula I are C$_1$–C$_5$-alkylthio, substituted or unsubstituted phenoxy, halogen, in particular chlorine or bromine, hydroxyl, amino, C$_1$–C$_4$-mono- or dialkylamino, pyrrolidino, piperidino, morpholino, thiomorpholino, piperazino, N-(C$_1$–C$_4$-alkyl)piperazino, C$_1$–C$_5$-alkoxycarbonyl or substituted or unsubstituted phenyl.

Examples of suitable substituents for alkenyls, alkynyls or cycloalkyls in the formula I are fluorine, chlorine or bromine.

When T$^2$ and T$^3$ together with the nitrogen linking them are a 5- to 7-membered saturated heterocyclic radical which can contain further hetero atoms, suitable examples are pyrrolidino, piperidino, morpholino, thiomorpholino, thiomorpholino S,S-dioxide, piperazino, N-(C$_1$–C$_4$-alkyl)piperazino or hexamethyleneimino.

Examples of T$^1$, T$^2$, T$^3$ and T$^4$ are methyl, ethyl, propyl, isopropyl, butyl, isobutyl or sec-butyl.

Examples of R$^4$ are formyl, acetyl, propionyl, butyryl, isobutyryl, pentanoyl or hexanoyl.

(The names isooctyl, isononyl, isodecyl and isotridecyl used hereinafter are trivial names derived from the alcohols obtained in the oxo synthesis (cf. Ullmanns Encyklopädie der technischen Chemie, 4th edition, volume 7, pages 215 to 217, and volume 11, pages 435 and 436.)

—NX is derived from primary amines of the formula H$_2$NX. Examples of these which may be mentioned are methylamine, ethylamine, propylamine, isopropylamine, butylamine, isobutylamine, sec-butylamine, tert-butylamine, pentylamine, isopentylamine, neopentylamine, hexylamine, heptylamine, n-octylamine, isooctylamine, 2-ethylhexylamine, nonylamine, isononylamine, decylamine, isodecylamine, undecylamine, dodecylamine, tridecylamine, isotridecylamine, tetradecylamine, pentadecylamine, hexadecylamine, heptadecylamine, octadecylamine, nonadecylamine, eicosylamine, allylamine, methallylamine, propargylamine, cyclopropylamine, cyclobutylamine, cyclopentylamine, cyclohexylamine, cycloheptylamine, cyclooctylamine, cyclononylamine, cyclodecylamine, 2-hydroxyethylamine, 2-methoxyethylamine, 2-ethoxyethylamine, 3-hydroxypropylamine, 3-methoxypropylamine, 3-ethoxypropylamine, 3-(2-phenoxyethoxy)-propylamine, 3-benzyloxypropylamine, 2-(N,N-dimethylamino)ethylamine, 2-(N,N-diethylamino)ethylamine, 3-(N,N-dimethylamino)propylamine, 3-(N,N-diethylamino)propylamine, benzylamine, 2-phenylethylamine, 3-phenylpropylamine, aniline, 2-hydroxyaniline, 3-hydroxyaniline, 4-hydroxyaniline, o-anisidine, m-anisidine, p-anisidine, o-phenetidine, m-phenetidine, p-phenetidine, 2-chloroaniline, 3-chloroaniline, 3-nitroaniline, 4-nitroaniline, o-toluidine, m-toluidine, p-toluidine, 1,2-phenylenediamine, 1,3-phenylenediamine, 1,4-phenylenediamine, 2-ethylaniline, 3-ethylaniline, 4-ethylaniline, 2-aminopyridine, 3-aminopyridine, 4-aminopyridine, glycine methyl ester, glycine ethyl ester, glycine propyl ester, glycine butyl ester, hydrazine, N,N-dimethylhydrazine or phenylhydrazine.

$T^5$ is derived from, for example, active methylene compounds of the formula $H_2T^5$. Compounds of this type have, for example, the formula

where Z is cyano, nitro, $C_1-C_6$-alkanoyl, benzoyl, $C_1-C_4$-alkylsulfonyl, phenylsulfonyl, carboxyl, $C_1-C_4$-alkoxycarbonyl, carbamoyl or $C_1-C_4$-mono- or dialkylcarbamoyl, or the formulae

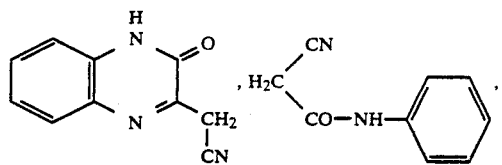

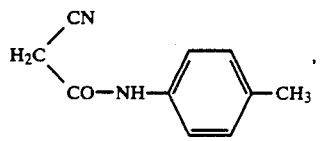

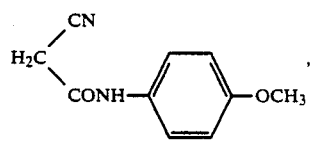

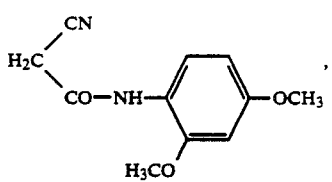

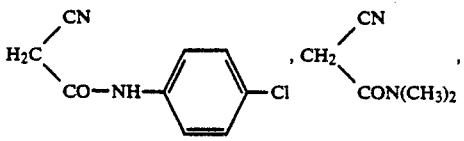

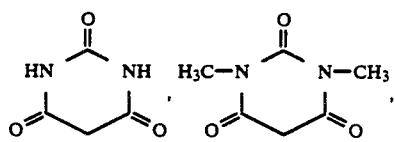

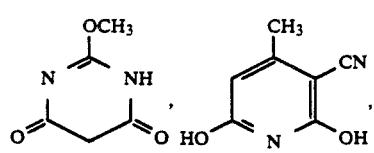

-continued

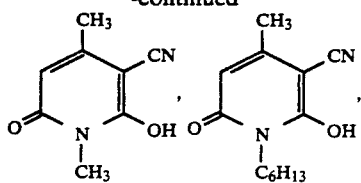

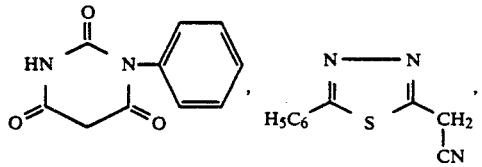

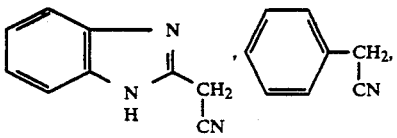

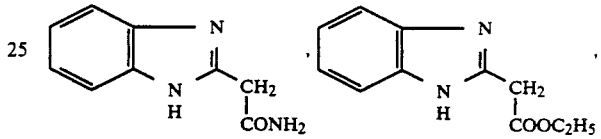

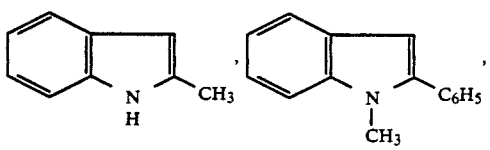

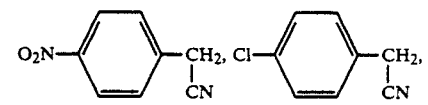

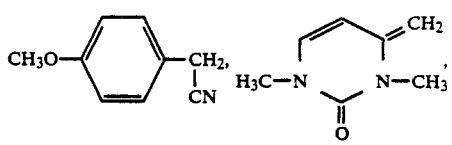

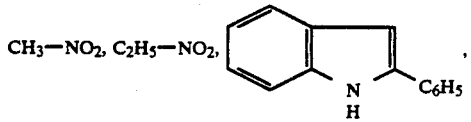

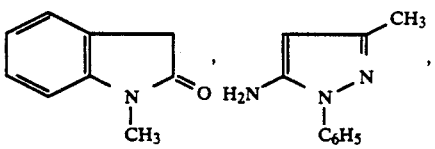

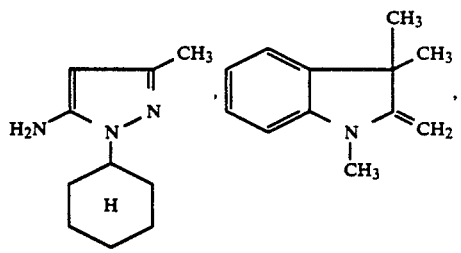

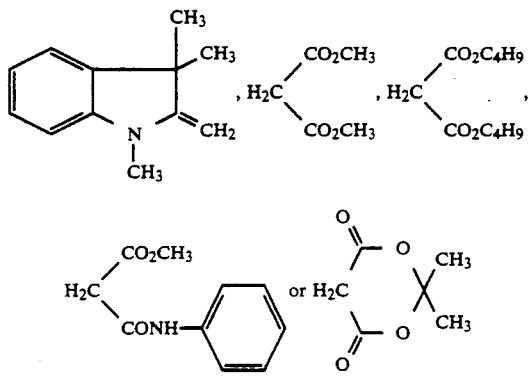

Examples of some particularly important compounds are:

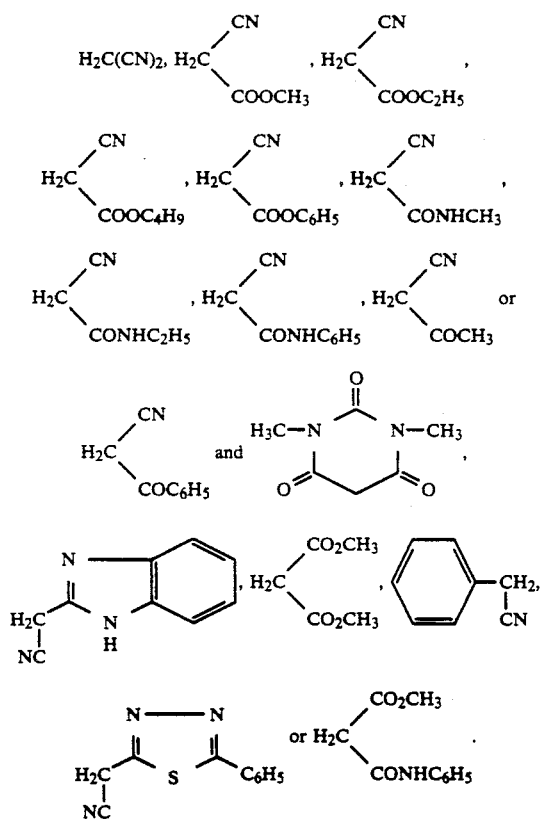

Examples of $R^3$ are methylamino, ethylamino, propylamino, isopropylamino, butylamino, isobutylamino, sec-butylamino, pentylamino, isopentylamino, neopentylamino, hexylamino, heptylamino, octylamino, isooctylamino, 2-ethylhexylamino, nonylamino, isononylamino, decylamino, isodecylamino, undecylamino, dodecylamino, tridecylamino, isotridecylamino, tetradecylamino, pentadecylamino, hexadecylamino, heptadecylamino, octadecylamino, nonadecylamino, eicosylamino, allylamino, propargylamino, methallylamino, cyclopropylamino, cyclobutylamino, cyclopentylamino, cyclohexylamino, cycloheptylamino, cyclooctylamino, cyclononylamino, cyclodecylamino, 2-hydroxyethylamino, 2-methoxyethylamino, 2-ethoxyethylamino, 2-benzyloxyethylamino, 3-hydroxypropylamino, 3-methoxypropylamino, 3-ethoxypropylamino, 3-(2-phenoxyethoxy)propylamino, 3-benzyloxypropylamino, 2-aminoethylamino, 2-(N,N-dimethylamino)ethylamino, 2-(N,N-diethylamino)ethylamino, 3-(N,N-dimethylamino)propylamino, 3-(N,N-diethylamino)propylamino, benzylamino, 2-phenylethylamino, 1-phenylethylamino, phenylamino, 2-hydroxyphenylamino, 3-hydroxyphenylamino, 4-hydroxyphenylamino, 2-methoxyphenylamino, 3-methoxyphenylamino, 4-methoxyphenylamino, 2-ethoxyphenylamino, 3-ethoxyphenylamino, 4-ethoxyphenylamino, 2-chlorophenylamino, 3-chlorophenylamino, 4-chlorophenylamino, 2-nitrophenylamino, 3-nitrophenylamino, 4-nitrophenylamino, 2-aminophenylamino, 3-aminophenylamino, 4-aminophenylamino, 2-methylphenylamino, 3-methylphenylamino, 4-methylphenylamino, 2-ethylphenylamino, 3-ethylphenylamino, 4-ethylphenylamino, 2-pyridylamino, 3-pyridylamino, 4-pyridylamino, methoxycarbonylmethylamino, ethoxycarbonylmethylamino, propoxycarbonylmethylamino, butoxycarbonylmethylamino, 2-methoxycarbonylmethylamino, 2-ethoxycarbonylmethylamino, 2-propoxycarbonylmethylamino, 2-butoxycarbonylmethylamino, 2-(3,4-dichlorophenyl)ethylamino, 2-(3-chloro-2-methylphenyl)ethylamino, 2-(3,4-dimethoxyphenyl)ethylamino, 2-(2-chlorophenyl)ethylamino, 2-thienylamino, dimethylamino, diethylamino, dipropylamino, dibutylamino, diallylamino, N-methyl-N-butylamino, N-methyl-N-phenylamino, N-methyl-N-benzylamino, N-ethyl-N-benzylamino, 3-morpholinopropylamino, 2-(1-piperazinyl)ethylamino, phenoxyethylamino, phenoxypropylamino, 2-methylthioethylamino, 3-methylthiopropylamino, 2-ethylthioethylamino, 3-ethylthiopropylamino, 2-aminoethylamino, 3-aminopropylamino, 2-dimethylaminoethylamino, 3-dimethylaminopropylamino, 2-diethylaminoethylamino, 3-diethylaminopropylamino, diethanolamino, N-ethyl-N-phenylamino, dibenzylamino, N-methylpiperazino, 2-pyrrolidinoethylamino, 2-piperidinoethylamino, 2-morpholinoethylamino, 2-thiomorpholinoethylamino, 2-hexamethyleneiminoethylamino, 2-(N-methylpiperazino)ethylamino, hydrazino, N-methylhydrazino, N-ethylhydrazino, phenylhydrazino, N,N-dimethylhydrazino, N,N-diethylhydrazino, N,N'-dimethylhydrazino, N,N'-diethylhydrazino, N,N-dipropylhydrazino, N,N-dibutylhydrazino, 1-imidazolyl, 1-pyrazolyl, 2,4-dimethylphenylamino, 3-dimethylaminophenylamino, 4-cyanophenylamino, 2-carboxyphenylamino, 4-acetylphenylamino or 2,4-dichlorophenylamino.

Preferred diaminothiophenes of the formula I are those in which $R^1$ and $R^2$ are each hydrogen or together are

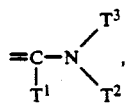

where $T^1$ is hydrogen, $C_1$–$C_4$-alkyl or phenyl, and $T^2$ and $T^3$ are, independently of one another, $C_1$–$C_4$-alkyl or phenyl, or together with the nitrogen linking them are pyrrolidino, piperidino, morpholino, thiomorpholino, piperazino, N-($C_1$–$C_4$-alkyl)piperazino or hexamethyleneimino, and $R^3$ and $R^4$ each have the abovementioned meanings.

Particularly preferred diaminothiophenes of the formula I are those in which $R^1$ and $R^2$ are each hydrogen or together are

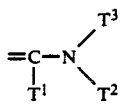

where $T^1$ is hydrogen and $T^2$ and $T^3$ are, independently of one another, $C_1-C_4$-alkyl.

Further particularly preferred diaminothiophenes of the formula I are those in which
$R^4$ is formyl, acetyl, propionyl, butyryl, benzoyl, cyano, nitro or

where $T^4$ is hydrogen, methyl, ethyl or phenyl, and $T^5$ has the abovementioned meaning.

Further particularly preferred diaminothiophenes of the formula I are those in which $R^3$ is $C_1-C_6$-mono- or dialkylamino, allylamino, methallylamino, propargylamino, $C_2-C_6$-alkylamino which is substituted by phenyl, hydroxyl, phenoxy, amino or $C_1-C_4$-mono- or dialkylamino or interrupted by an oxygen, or phenylamino, pyrrolidino, piperidino, morpholino, piperazino or N-($C_1-C_4$-alkyl)piperazino.

Further particularly preferred diaminothiophenes of the formula I are those in which $R^4$ is cyano, nitro, formyl or

where Z is cyano, nitro or $C_1-C_4$-alkoxycarbonyl.

Especially important are diaminothiophenes of the formula I in which $R^1$ and $R^2$ are each hydrogen or together are $=CH-N(CH_3)_2$.

Very particularly important are diaminothiophenes of the formula Ia

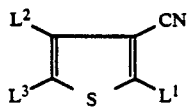

or tautomers thereof, where
$L^1$ is amino,
$L^2$ is $C_1-C_6$-mono- or dialkylamino, allylamino, methallylamino, propargylamino, $C_2-C_6$-alkylamino which is substituted by phenyl, hydroxyl, phenoxy, amino or $C_1-C_4$-mono- or dialkylamino or interrupted by an oxygen, or phenylamino, pyrrolidino, piperidino, morpholino, piperazino or N-($C_1-C_4$-alkyl)piperazino and
$L^3$ is cyano, nitro, formyl or

where Z is cyano, nitro or $C_1-C_4$-alkoxycarbonyl.

The diaminothiophenes of the formula I according to the invention can be obtained, for example, by reaction of aminothiophenes of the formula II

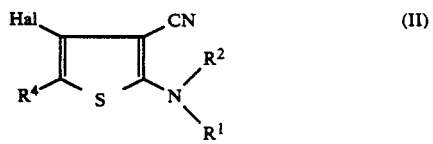

where $R^1$, $R^2$ and $R^4$ each has the abovementioned meaning, and Hal is chlorine or bromine, with an amino compound of the formula III

where $R^3$ has the abovementioned meaning.

This entails, for example, the aminothiophene II being reacted with the amino compound III in an inert solvent (e.g. N,N-dimethylformamide, N,N-dimethylacetamide, N-methylpyrrolidone, hexamethylphosphoric trisamide, 1,3-dimethylimidazolin-2-one, 1,3-dimethylhexylhydropyrimidin-2-one or 1,2-diethoxyethane) at from $-10°$ to $+150°$ C. The molar ratio II:III is usually 1:2 to 1:10.

The aminothiophenes of the formula II have been disclosed, for example, in EP-A 193,885 or can be obtained by methods similar to those detailed therein.

The novel diaminothiophenes are valuable intermediates for the synthesis of dyes, crop protection agents or pharmaceuticals. They are especially used as diazo components ($R^1$ and $R^2$=H) for the preparation of azo dyes.

The Examples which follow are intended to illustrate the invention in detail.

EXAMPLE 1

2-Amino-3,5-dicyano-4-piperidinothiophene 4,6 g of 2-amino-4-chloro-3,5-dicyanothiophene were dissolved in 25 ml of N,N-dimethylformamide (DMF). 5.3 g of piperidine were added dropwise to this at room temperature, and the mixture was stirred at room temperature for 4 hours. The reaction mixture was then stirred into 800 g of water. The precipitate was filtered off with suction, washed with water and dried in an oven at 50° C. 5.4 g (93% of theory) of the compound of the formula

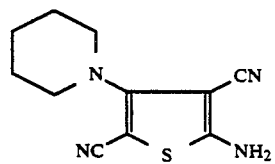

were obtained with melting point 183° to 184° C. The NMR, IR, UV and mass spectra and the elemental analysis are consistent with the structure indicated above.

The compounds listed in the following table are obtained in a similar manner.

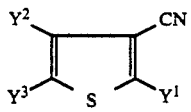

| Ex. No. | $Y^1$ | $Y^2$ | $Y^3$ | Melting point [°C.] |
|---|---|---|---|---|
| 2 | $NH_2$ | $NHCH_3$ | CN | |
| 3 | $NH_2$ | $NH-C_2H_5$ | CN | |
| 4 | $NH_2$ | $NH-n-C_3H_7$ | CN | 177–180 |
| 5 | $NH_2$ | $NH-iso-C_3H_7$ | CN | 170–171 |
| 6 | $NH_2$ | $NH-n-C_4H_9$ | CN | 211–212 |
| 7 | $NH_2$ | $NH-sec-C_4H_9$ | CN | 121–126 |
| 8 | $NH_2$ | $NH-iso-C_4H_9$ | CN | 178 |
| 9 | $NH_2$ | $NH-tert-C_4H_9$ | CN | 139–142 |
| 10 | $NH_2$ | $NH-n-C_5H_{11}$ | CN | 177–178 |
| 11 | $NH_2$ | $NH-iso-C_5H_{11}$ | CN | |
| 12 | $NH_2$ | $NH-neo-C_5H_{11}$ | CN | |
| 13 | $NH_2$ | $NH-n-C_6H_{13}$ | CN | |
| 14 | $NH_2$ | $NH-n-C_7H_{15}$ | CN | 92–97 |
| 15 | $NH_2$ | $NH-n-C_8H_{17}$ | CN | |
| 16 | $NH_2$ | $NH-n-C_9H_{19}$ | CN | |
| 17 | $NH_2$ | $NH-n-C_{10}H_{21}$ | CN | |
| 18 | $NH_2$ | $NH-n-C_{11}H_{23}$ | CN | |
| 19 | $NH_2$ | $NH-n-C_{12}H_{25}$ | CN | |
| 20 | $NH_2$ | $NH-n-C_{13}H_{27}$ | CN | |
| 21 | $NH_2$ | $NH-n-C_{14}H_{29}$ | CN | |
| 22 | $NH_2$ | $NH-n-C_{15}H_{31}$ | CN | |
| 23 | $NH_2$ | $NH-n-C_{16}H_{33}$ | CN | |
| 24 | $NH_2$ | $NH-n-C_{17}H_{35}$ | CN | |
| 25 | $NH_2$ | $NH-n-C_{18}H_{37}$ | CN | |
| 26 | $NH_2$ | $NH-n-C_{19}H_{39}$ | CN | |
| 27 | $NH_2$ | $NH-n-C_{20}H_{41}$ | CN | |
| 28 | $NH_2$ | $NH-CH_2-CH=CH_2$ | CN | |
| 29 | $NH_2$ | $NH-CH_2-C\equiv CH$ | CN | |
| 30 | $NH_2$ | $NH-CH_2-CH=CH-CH_3$ | CN | |
| 31 | $NH_2$ | $NH-CH_2-CH_2-OH$ | CN | 170 |
| 32 | $NH_2$ | $NH-CH_2-CH_2-OCH_3$ | CN | |
| 33 | $NH_2$ | $NH-CH_2-CH_2-OC_2H_5$ | CN | 175 |
| 34 | $NH_2$ | $NH-CH_2-CH_2-O-nC_3H_7$ | CN | |
| 35 | $NH_2$ | $NH-CH_2-CH_2-OC_6H_5$ | CN | |
| 36 | $NH_2$ | $NH-CH_2-CH_2-OCH_2-C_6H_5$ | CN | |
| 37 | $NH_2$ | $NH-CH_2-CH_2-NH_2$ | CN | |
| 38 | $NH_2$ | $NH-CH_2-CH_2-N(CH_3)_2$ | CN | |
| 39 | $NH_2$ | $NH-CH_2-CH_2-N(C_2H_5)_2$ | CN | 125–129 |
| 40 | $NH_2$ | $NH-(CH_2)_3-OH$ | CN | 171–172 |
| 41 | $NH_2$ | $NH-(CH_2)_3-OCH_3$ | CN | |
| 42 | $NH_2$ | $NH-(CH_2)_3-OC_2H_5$ | CN | |
| 43 | $NH_2$ | $NH-(CH_2)_3-O-n-C_3H_7$ | CN | |
| 44 | $NH_2$ | $NH-(CH_2)_3-OC_6H_5$ | CN | |
| 45 | $NH_2$ | $NH-(CH_2)_3-OCH_2C_6H_5$ | CN | |
| 46 | $NH_2$ | $NH-(CH_2)_3-O(CH_2)_2-OC_6H_5$ | CN | |
| 47 | $NH_2$ | $NH-(CH_2)_3-NH_2$ | CN | |
| 48 | $NH_2$ | $NH-(CH_2)_3-N(CH_3)_2$ | CN | |
| 49 | $NH_2$ | $NH-(CH_2)_3-N(C_2H_5)_2$ | CN | |
| 50 | $NH_2$ | $NH-C_6H_5$ | CN | |
| 51 | $NH_2$ | $NH-CH_2C_6H_5$ | CN | |
| 52 | $NH_2$ | $NH-CH_2CH_2C_6H_5$ | CN | |
| 53 | $NH_2$ | $NH-CH_2(CH_3)C_6H_5$ | CN | |
| 54 | $NH_2$ | $NH-cyclo-C_3H_5$ | CN | |
| 55 | $NH_2$ | $NH-cyclo-C_4H_7$ | CN | |
| 56 | $NH_2$ | $NH-cyclo-C_5H_9$ | CN | |
| 57 | $NH_2$ | $NH-cyclo-C_6H_{11}$ | CN | |
| 58 | $NH_2$ | $NH-cyclo-C_7H_{13}$ | CN | |
| 59 | $NH_2$ | $NH-cyclo-C_8H_{15}$ | CN | |
| 60 | $NH_2$ | $NH-CH_2-CH_2-SCH_3$ | CN | |
| 61 | $NH_2$ | $NH-CH_2-CH_2-SC_2H_5$ | CN | |
| 62 | $NH_2$ | $NH-(CH_2)_3SCH_3$ | CN | |
| 63 | $NH_2$ | $NH-(CH_2)_3SC_2H_5$ | CN | |
| 64 | $NH_2$ | $NH-C_6H_4-(2)-CH_3$ | CN | |
| 65 | $NH_2$ | $NH-C_6H_4-(3)-CH_3$ | CN | |
| 66 | $NH_2$ | $NH-C_6H_4-(4)-CH_3$ | CN | |
| 67 | $NH_2$ | $NH-C_6H_4-(2)-C_2H_5$ | CN | |
| 68 | $NH_2$ | $NH-C_6H_4-(3)-C_2H_5$ | CN | |
| 69 | $NH_2$ | $NH-C_6H_4-(4)-C_2H_5$ | CN | |
| 70 | $NH_2$ | $NH-C_6H_4-(2)-OH$ | CN | |
| 71 | $NH_2$ | $NH-C_6H_4-(3)-OH$ | CN | |
| 72 | $NH_2$ | $NH-C_6H_4-(4)-OH$ | CN | |
| 73 | $NH_2$ | $NH-C_6H_4-(2)-Cl$ | CN | |
| 74 | $NH_2$ | $NH-C_6H_4-(3)-Cl$ | CN | |
| 75 | $NH_2$ | $NH-C_6H_4-(4)-Cl$ | CN | |
| 76 | $NH_2$ | $NH-C_6H_4-(2)-OCH_3$ | CN | |

-continued

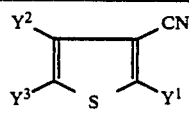

| Ex. No. | $Y^1$ | $Y^2$ | $Y^3$ | Melting point [°C.] |
|---|---|---|---|---|
| 77 | $NH_2$ | $NH-C_6H_4-(3)-OCH_3$ | CN | |
| 78 | $NH_2$ | $NH-C_6H_4-(4)-OCH_3$ | CN | |
| 79 | $NH_2$ | $NH-C_6H_4-(2)-OC_2H_5$ | CN | |
| 80 | $NH_2$ | $NH-C_6H_4-(3)-OC_2H_5$ | CN | |
| 81 | $NH_2$ | $NH-C_6H_4-(4)-OC_2H_5$ | CN | |
| 82 | $NH_2$ | $NH-C_6H_4-(2)-NH_2$ | CN | |
| 83 | $NH_2$ | $NH-C_6H_4-(3)-NH_2$ | CN | |
| 84 | $NH_2$ | $NH-C_6H_4-(4)-NH_2$ | CN | |
| 85 | $NH_2$ | $NH-C_6H_3-(2,3)-(CH_3)_2$ | CN | |
| 86 | $NH_2$ | $NH-C_6H_3-(2,4)-(CH_3)_2$ | CN | |
| 87 | $NH_2$ | $NH-C_6H_3-(2,5)-(CH_3)_2$ | CN | |
| 88 | $NH_2$ | $NH-C_6H_3-(2,6)-(CH_3)_2$ | CN | |
| 89 | $NH_2$ | $NH-C_6H_3-(3,4)-(CH_3)_2$ | CN | |
| 90 | $NH_2$ | $NH-C_6H_3-(3,5)-(CH_3)_2$ | CN | |
| 91 | $NH_2$ | $NH-C_6H_4-(2)-N(CH_3)_2$ | CN | |
| 92 | $NH_2$ | $NH-C_6H_4-(3)-N(CH_3)_2$ | CN | |
| 93 | $NH_2$ | $NH-C_6H_4-(4)-N(CH_3)_2$ | CN | |
| 94 | $NH_2$ | $NH-C_6H_4-(2)-CN$ | CN | |
| 95 | $NH_2$ | $NH-C_6H_4-(3)-CN$ | CN | |
| 96 | $NH_2$ | $NH-C_6H_4-(4)-CN$ | CN | |
| 97 | $NH_2$ | $NH-C_6H_4-(2)-COOH$ | CN | |
| 98 | $NH_2$ | $NH-C_6H_4-(3)-COOH$ | CN | |
| 99 | $NH_2$ | $NH-C_6H_4-(4)-COOH$ | CN | |
| 100 | $NH_2$ | $NH-C_6H_4-(2)-CO-CH_3$ | CN | |
| 101 | $NH_2$ | $NH-C_6H_4-(3)-CO-CH_3$ | CN | |
| 102 | $NH_2$ | $NH-C_6H_4-(4)-CO-CH_3$ | CN | |
| 103 | $NH_2$ | $NH-C_6H_4-(2,3)-Cl_2$ | CN | |
| 104 | $NH_2$ | NH-pyrid-2-yl | CN | |
| 105 | $NH_2$ | NH-pyrid-3-yl | CN | |
| 106 | $NH_2$ | NH-pyrid-4-yl | CN | |
| 107 | $NH_2$ | NH-thien-2-yl | CN | |
| 108 | $NH_2$ | $N(CH_3)_2$ | CN | |
| 109 | $NH_2$ | $N(C_2H_5)_2$ | CN | |
| 110 | $NH_2$ | $N(n-C_3H_7)_2$ | CN | |
| 111 | $NH_2$ | $N(n-C_4H_9)_2$ | CN | |
| 112 | $NH_2$ | $N(CH_2CH=CH_2)_2$ | CN | |
| 113 | $NH_2$ | $N(CH_3)(C_6H_5)$ | CN | |
| 114 | $NH_2$ | $N(C_2H_5)(CH_2C_6H_5)$ | CN | |
| 115 | $NH_2$ | $N(CH_3)(C_6H_5)$ | CN | |
| 116 | $NH_2$ | $N(C_2H_5)(CH_2C_6H_5)$ | CN | |
| 117 | $NH_2$ | $N(CH_2C_6H_5)_2$ | CN | |
| 118 | $NH_2$ | $N(CH_2CH_2OH)_2$ | CN | |
| 119 | $NH_2$ | N-pyrazolyl | CN | |
| 120 | $NH_2$ | N-imidazolyl | CN | |
| 121 | $NH_2$ | N-pyrrolidinyl | CN | |
| 122 | $NH_2$ | N-hexamethyleneimino | CN | |
| 123 | $NH_2$ | N-morpholinyl | CN | |

-continued structure: thiophene ring with Y² at 4-position, CN at 3-position, Y³ at 5-position, Y¹ at 2-position

| Ex. No. | Y¹ | Y² | Y³ | Melting point [°C.] |
|---|---|---|---|---|
| 124 | $NH_2$ | −N(CH₂CH₂)₂S (thiomorpholino) | CN | |
| 125 | $NH_2$ | −N(CH₂CH₂)₂NH (piperazinyl) | CN | |
| 126 | $NH_2$ | −N(CH₂CH₂)₂N−CH₃ (4-methylpiperazinyl) | CN | |
| 127 | $NH_2$ | NH−(CH₂)₂−N(pyrrolidinyl) | CN | |
| 128 | $NH_2$ | NH−(CH₂)₂−N(piperidinyl) | CN | |
| 129 | $NH_2$ | NH−(CH₂)₂−N(hexamethyleneimino) | CN | |
| 130 | $NH_2$ | NH−(CH₂)₂−N(morpholino) | CN | |
| 131 | $NH_2$ | NH−(CH₂)₂−N(thiomorpholino) | CN | |
| 132 | $NH_2$ | NH−(CH₂)₂−N(CH₂CH₂)₂N−CH₃ | CN | |
| 133 | $NH_2$ | NH−(CH₂)₃−N(morpholino) | CN | |
| 134 | $NH_2$ | $NH-NH_2$ | CN | |
| 135 | $NH_2$ | $NH-N(CH_3)_2$ | CN | |
| 136 | $NH_2$ | $NH-NH-C_6H_5$ | CN | |
| 137 | $NH_2$ | $NH-NH-CH_3$ | CN | |
| 138 | $NH_2$ | $N(CH_3)-NH-CH_3$ | CN | |
| 139 | $NH_2$ | $NH-N(C_2H_5)_2$ | CN | |
| 140 | $NH_2$ | $NH-N(n-C_3H_7)_2$ | CN | |
| 141 | $NH_2$ | $NH-N(n-C_4H_9)_2$ | CN | |
| 142 | $N=CH-N(CH_3)_2$ | $N(C_2H_5)_2$ | CN | |
| 143 | $N=CH-N(CH_3)_2$ | $N(CH_3)_2$ | CN | |
| 144 | $N=CH-N(C_2H_5)_2$ | $N(CH_3)_2$ | CN | |
| 145 | $N=CH-N(C_2H_5)_2$ | $N(C_2H_5)_2$ | CN | |
| 146 | $NH_2$ | $NH-CH_3$ | $NO_2$ | |
| 147 | $NH_2$ | $NH-C_2H_5$ | $NO_2$ | |
| 148 | $NH_2$ | $NH-n-C_3H_7$ | $NO_2$ | |

-continued

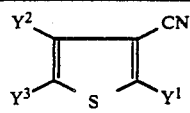

| Ex. No. | Y$^1$ | Y$^2$ | Y$^3$ | Melting point [°C.] |
|---|---|---|---|---|
| 149 | NH$_2$ | NH-iso-C$_3$H$_7$ | NO$_2$ | |
| 150 | NH$_2$ | NH-n-C$_4$H$_9$ | NO$_2$ | |
| 151 | NH$_2$ | NH-n-C$_5$H$_{11}$ | NO$_2$ | |
| 152 | NH$_2$ | NH-cyclo-C$_3$H$_5$ | NO$_2$ | |
| 153 | NH$_2$ | NH-cyclo-C$_6$H$_{11}$ | NO$_2$ | |
| 154 | NH$_2$ | pyrrolidin-1-yl | NO$_2$ | >315 |
| 155 | NH$_2$ | piperidin-1-yl | NO$_2$ | |
| 156 | NH$_2$ | azepan-1-yl | NO$_2$ | |
| 157 | NH$_2$ | morpholin-4-yl | NO$_2$ | 275–276 |
| 158 | NH$_2$ | piperazin-1-yl | NO$_2$ | |
| 159 | NH$_2$ | NH—CH$_3$ | CH=N—CH$_3$ | |
| 160 | NH$_2$ | NH—C$_2$H$_5$ | CH=N—C$_2$H$_5$ | |
| 161 | NH$_2$ | N(CH$_3$)$_2$ | CHO | |
| 162 | NH$_2$ | N(C$_2$H$_5$)$_2$ | CHO | |
| 163 | NH$_2$ | N(n-C$_3$H$_7$)$_2$ | CHO | |
| 164 | NH$_2$ | N(n-C$_4$H$_9$)$_2$ | CHO | |
| 165 | NH$_2$ | pyrrolidin-1-yl | CHO | |
| 166 | NH$_2$ | piperidin-1-yl | CHO | |
| 167 | NH$_2$ | azepan-1-yl | CHO | |
| 168 | NH$_2$ | morpholin-4-yl | CHO | |
| 169 | NH$_2$ | thiomorpholin-4-yl | CHO | |

-continued $$\begin{array}{c} Y^2 \quad CN \\ Y^3 \diagup S \diagdown Y^1 \end{array}$$

| Ex. No. | Y¹ | Y² | Y³ | Melting point [°C.] |
|---|---|---|---|---|
| 170 | NH₂ | piperazine (N−NH ring) | CHO | |
| 171 | NH₂ | N-methylpiperazine (N−N−CH₃ ring) | CHO | |
| 172 | NH₂ | N(CH₃)₂ | CO−CH₃ | |
| 173 | NH₂ | N(C₂H₅)₂ | CO−CH₃ | |
| 174 | NH₂ | N(CH₃)₂ | CO−C₂H₅ | |
| 175 | NH₂ | N(C₂H₅)₂ | CO-n-C₃H₇ | |
| 176 | NH₂ | N(CH₃)₂ | CO-iso-C₃H₇ | |
| 177 | NH₂ | N(CH₃)₂ | CO−C₆H₅ | |
| 178 | NH₂ | N(CH₃)₂ | CH=C(CN)₂ | |
| 179 | NH₂ | N(C₂H₅)₂ | CH=C(CN)₂ | 107−109 |
| 180 | NH₂ | N(n-C₃H₇)₂ | CH=C(CN)₂ | |
| 181 | NH₂ | N(n-C₄H₉)₂ | CH=C(CN)₂ | |
| 182 | NH₂ | pyrrolidino (N ring) | CH=C(CN)₂ | |
| 183 | NH₂ | piperidino (N ring) | CH=C(CN)₂ | 225 |
| 184 | NH₂ | hexamethyleneimino (N ring) | CH=C(CN)₂ | |
| 185 | NH₂ | morpholino (N−O ring) | CH=C(CN)₂ | 270 |
| 186 | NH₂ | NH−CH(C₆H₅)₂ | CH=C(CN)(C₆H₅) | |
| 187 | NH₂ | NH−CH₃ | CH=C(NO₂)(CH₃) | |
| 188 | NH₂ | NH−C₂H₅ | CH=C(NO₂)(H) | |
| 189 | NH₂ | NH−C₆H₅ | CH=C(CN)(NH−C₆H₅) | |

-continued

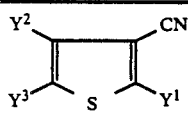

| Ex. No. | $Y^1$ | $Y^2$ | $Y^3$ | Melting point [°C.] |
|---|---|---|---|---|
| 190 | $NH_2$ | $N(C_2H_5)_2$ | $CH=C(CN)(CO_2C_2H_5)$ | |
| 191 | $NH_2$ | morpholino (N-O ring) | $CH=C(CN)(CO_2CH_3)$ | |
| 192 | $NH_2$ | $NH-CH_3$ | $CH=C(CN)(CONHCH_3)$ | |
| 193 | $NH_2$ | $NH-C_2H_5$ | $CH=C(CN)(CONHC_2H_5)$ | |
| 194 | $NH_2$ | piperidino | $CH=C(CN)(CO-CH_3)$ | |
| 195 | $NH_2$ | piperidino | $CH=C(CN)(CO-C_6H_5)$ | |
| 196 | $NH_2$ | morpholino | $CH=$ (1,3-dimethylbarbituric acid ylidene) | |
| 197 | $NH_2$ | $NHCH_3$ | $CH=C(CN)(C(=N-)NH-)$ benzimidazoline | |
| 198 | $NH_2$ | $NHC_2H_5$ | $CH=C(CO_2CH_3)_2$ | |
| 199 | $NH_2$ | $N(CH_3)_2$ | $CH=C(CN)$-(5-phenyl-1,3,4-thiadiazol-2-yl) | |
| 200 | $NH_2$ | $NH-C_6H_5$ | $CH=C(CO_2C_6H_5)(CONHC_6H_5)$ | |

We claim:
1. A diaminothiophene of Formula I:

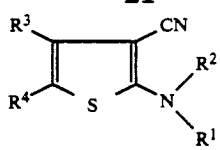 (I)

or tautomers thereof, wherein $R^1$ and $R^2$ are each hydrogen, $R^3$ is $C_1$–$C_{20}$-mono- or dialkylamino, $C_2$–$C_{10}$-mono or dialkylamino whose alkyl is substituted and/or interrupted by one or more oxygen atoms, $C_2$–$C_{12}$-mono- or dialkenylamino, $C_3$–$C_{12}$-alkynylamino, N-($C_1$–$C_5$-alkyl)-N-phenylamino, hydrazino, $C_1$–$C_4$-mono- or dialkylhydrazino or phenylhydrazino, and $R^4$ $C_1$–$C_6$-alkanoyl, benzoyl, cyano, nitro or

where $T^4$ is hydrogen, $C_1$–$C_4$-alkyl or phenyl, and $T^5$ is the radical of an active methylene compound, or hydroxyimino or N-X where X is $C_1$–$C_{20}$-alkyl which can be substituted and/or interrupted by one or more oxygens, substituted or unsubstituted $C_3$–$C_6$-alkenyl, substituted or unsubstituted $C_3$–$C_6$-alkynyl, substituted or unsubstituted $C_3$–$C_{10}$-cycloalkyl, substituted or unsubstituted phenyl, pyridyl, $C_1$–$C_4$-alkoxycarbonylmethyl, amino, $C_1$–$C_4$-dialkylamino or phenylamino.

* * * * *